(12) United States Patent
Curtis et al.

(10) Patent No.: US 11,250,973 B2
(45) Date of Patent: Feb. 15, 2022

(54) ELECTROSURGICAL DEVICE POWER CABLE

(71) Applicant: GYRUS ACMI, INC., Southborough, MA (US)

(72) Inventors: Richard J. Curtis, Corcoran, MN (US); William F. Kratoska, Plymouth, MN (US); Jeffrey J. Nelson, Plymouth, MN (US); Theodore C. Blus, Shoreview, MN (US); Kester J. Batchelor, Mound, MN (US); Mark J. Kroll, Dresser, WI (US); Charles Wood, Eden Prairie, MN (US)

(73) Assignee: Gyms Acmi, Inc., Westborough, MA (US)

( * ) Notice: Subject to any disclaimer, the term of this patent is extended or adjusted under 35 U.S.C. 154(b) by 504 days.

(21) Appl. No.: 15/872,301

(22) Filed: Jan. 16, 2018

(65) Prior Publication Data

US 2018/0218808 A1 Aug. 2, 2018

Related U.S. Application Data

(60) Provisional application No. 62/451,952, filed on Jan. 30, 2017.

(51) Int. Cl.
*H01B 9/02* (2006.01)
*A61B 18/14* (2006.01)
(Continued)

(52) U.S. Cl.
CPC ........... *H01B 9/02* (2013.01); *A61B 18/1206* (2013.01); *A61B 18/1445* (2013.01);
(Continued)

(58) Field of Classification Search
CPC . A61B 18/1206; A61B 18/1445; A61B 18/16; A61B 2018/00178;
(Continued)

(56) References Cited

U.S. PATENT DOCUMENTS

| 5,007,908 A | 4/1991 | Rydell |
| 5,435,805 A * | 7/1995 | Edwards ................. A61N 1/06 |
| | | 604/22 |

(Continued)

FOREIGN PATENT DOCUMENTS

| CN | 103959398 A | 7/2014 |
| CN | 108376892 A | 8/2018 |

(Continued)

OTHER PUBLICATIONS

"Chinese Application Serial No. 201810082487.0, Office Action dated Mar. 14, 2019", w/o English Translation, 8 pgs.

(Continued)

*Primary Examiner* — Tigist S Demie
(74) *Attorney, Agent, or Firm* — Schwegman Landberg & Woessner, P.A.

(57) ABSTRACT

An electrosurgical device: (a) power cable comprising: (i) a primary lead that connects to a first pole of an AC power source and (ii) one or more auxiliary leads; wherein the power cable includes a dual core having the primary lead on a first side and the one or more auxiliary leads on a second side with a web being located between the first side and the second side.

13 Claims, 4 Drawing Sheets

(51) Int. Cl.
    *A61B 18/16*     (2006.01)
    *A61B 18/12*     (2006.01)
    *A61B 18/00*     (2006.01)

(52) U.S. Cl.
    CPC .... *A61B 18/16* (2013.01); *A61B 2018/00178* (2013.01); *A61B 2018/00196* (2013.01); *A61B 2018/00577* (2013.01); *A61B 2018/00589* (2013.01); *A61B 2018/00595* (2013.01); *A61B 2018/00607* (2013.01); *A61B 2018/00821* (2013.01); *A61B 2018/00922* (2013.01); *A61B 2018/126* (2013.01); *A61B 2018/1253* (2013.01); *A61B 2018/1293* (2013.01); *A61B 2018/1412* (2013.01); *A61B 2018/162* (2013.01); *A61B 2018/167* (2013.01)

(58) Field of Classification Search
    CPC ........... A61B 2018/00196; A61B 2018/00577; A61B 2018/00589; A61B 2018/00595; A61B 2018/00607; A61B 2018/00821; A61B 2018/00922; A61B 2018/01253; A61B 2018/126; A61B 2018/1293; A61B 2018/1412; A61B 2018/162; A61B 2018/167

See application file for complete search history.

(56) References Cited

U.S. PATENT DOCUMENTS

| | | | |
|---|---|---|---|
| 5,472,442 A * | 12/1995 | Klicek | A61B 18/1482 606/34 |
| 5,482,054 A | 1/1996 | Slater et al. | |
| 6,113,596 A | 9/2000 | Hooven et al. | |
| 6,190,386 B1 | 2/2001 | Rydell | |
| 6,494,877 B2 | 12/2002 | Odell et al. | |
| 7,232,440 B2 | 6/2007 | Dumbauld et al. | |
| 7,402,754 B2 | 7/2008 | Kirwan, Jr. et al. | |
| 7,722,607 B2 | 5/2010 | Dumbauld et al. | |
| 8,251,989 B1 | 8/2012 | Newton et al. | |
| 9,254,165 B2 | 2/2016 | Aronow et al. | |
| 2002/0128644 A1 | 9/2002 | Hata et al. | |
| 2003/0060816 A1 | 3/2003 | Iida | |
| 2004/0220561 A1* | 11/2004 | Kirwan, Jr. | A61B 18/12 606/41 |
| 2011/0054462 A1 | 3/2011 | Ellman | |
| 2012/0298395 A1* | 11/2012 | Gundel | H01R 13/5845 174/105 R |
| 2013/0178852 A1 | 7/2013 | Allen, IV et al. | |
| 2015/0105757 A1 | 4/2015 | Williams | |
| 2016/0199125 A1* | 7/2016 | Jones | A61B 18/1445 606/45 |

FOREIGN PATENT DOCUMENTS

| | | |
|---|---|---|
| CN | 108376892 | 11/2020 |
| EP | 0961298 A1 | 12/1999 |
| EP | 1532932 A1 | 5/2005 |
| EP | 1902681 A1 | 3/2008 |
| EP | 3354218 A2 | 8/2018 |
| JP | H11506676 A | 6/1999 |
| JP | 2002531215 A | 9/2002 |
| JP | 2018122089 A | 8/2018 |
| JP | 6587704 B2 | 9/2019 |
| RU | 159076 U1 | 1/2016 |
| WO | 98/06338 A2 | 2/1998 |

OTHER PUBLICATIONS

"Chinese Application Serial No. 201810082487.0, Office Action dated Oct. 23, 2019", w/English translation, 13 pgs.
"Chinese Application Serial No. 201810082487.0, Response filed Jul. 24, 2019 to Office Action dated Mar. 14, 2019", 37 pgs.
"Chinese Application Serial No. 201810082487.0, Response filed Dec. 30, 2019 to Office Action dated Oct. 23, 2019", w/ English Claims, 21 pgs.
"Chinese Application Serial No. 201810082487.0, Voluntary Amendment filed Nov. 28, 2018", 9 pgs.
"European Application Serial No. 18152279.8, Intention to Grant dated Apr. 1, 2020", 8 pgs.
"European Application Serial No. 18152279.8, Partial European Search Report dated Apr. 3, 2018", 12 pgs.
"European Application Serial No. 18152279.8, Response filed Feb. 8, 2019 to Extended European Search Report dated Jul. 26, 2018", 7 pgs.
"European Application Serial No. 18152279.8, Response filed Aug. 19, 2019 to Communication Pursuant to Article 94(3) EPC dated May 7, 2019", 11 pgs.
"Japanese Application Serial No. 2018-012479, Response filed Jul. 24, 2019 to Notification of Reasons for Refusal dated Feb. 26, 2019", w/o English Translation, 5 pgs.
JP Notification of Reasons for Refusal for JP2018-012479, dated Feb. 26, 2019.
CN Search Report for CN2018-10082487, dated Mar. 5, 2019.
CN Office Action for CN2018-10082487, dated Apr. 29, 2019.
EP Office Action for EP18152279, dated May 7, 2019.
European Search Report from the European Patent Office of Application No. 18152279 dated Jul. 26, 2018.
"Chinese Application Serial No. 201810082487.0, Office Action dated Apr. 8, 2020", w/English Translation, 8 pgs.
"Chinese Application Serial No. 201810082487.0, Response filed Jun. 18, 2020 to Office Action dated Apr. 8, 2020", w/ English Claims, 17 pgs.

* cited by examiner

ELECTROSURGICAL DEVICE POWER CABLE

FIELD

The present teachings generally relate to a power cable of an electrosurgical device that can supply both monopolar power and bipolar power during a surgical procedure without power from one cord within the power cable being transferred to another cord within the power cable in a sufficient amount that a disconnected part of the electrosurgical device is powered.

BACKGROUND

Typically, electrosurgical devices have stand-alone monopolar capabilities or bipolar capabilities and a single cord carries power to the electrosurgical device. Thus, a surgeon before a procedure begins may select either a device with monopolar capabilities or a device with bipolar capabilities and the surgeon can use the device to apply either monopolar power or bipolar power. For example, if the surgeon selects a monopolar device and monopolar power is not desired for the surgical procedure the surgeon may use either the device that supplies monopolar power to perform the procedure or switch to a device with bipolar capabilities. Both of these devices may be used to perform the procedure, however, switching between devices and/or using a device that may be better suited for a different purpose may disturb the procedure flow, cause unnecessary delays in the procedure, and in some cases result in less than optimal energy sources being used.

More recently, devices with dual capabilities have been produced. However, these devices have multiple power leads to supply multiple different types of power to an electrosurgical device. While one source of power is being supplied to an electrode an electrode that is off or disconnected may be capacitively coupled to the such that power may be transferred through the off or disconnected electrode.

Examples of some electrosurgical instruments may be found in U.S. Pat. Nos. 5,472,442; 6,113,596; 7,232,440; 7,722,607; and 8,251,989; and U.S. Patent Application Publication Nos. 2011/0054462 and 2013/0178852 all of which are incorporated by reference herein for all purposes. It would be attractive to have an electrosurgical device with a power cord that prevents capacitive coupling. It would be attractive to have an electrosurgical device that has a multi-core and each of the cores are separated by a web that spaces the cores apart. What is needed is an electrosurgical device where one or more of the leads have a portion that is covered by a shield so that the shield prevents power from transferring form a powered lead to a non-powered lead. What is needed is an electrosurgical device where the shield is electrically connected to a ground or a lead that is connected to a second pole of an AC power source so that power from an active lead is dissipated without being transferred to an off or disconnected lead. What is needed is an electrosurgical device with three or more leads and at least two of the leads are spaced a sufficient distance apart so that the leads are not capacitively coupled.

SUMMARY

The present teachings meet one or more of the present needs by providing: An electrosurgical device: (a) power cable comprising: (i) a primary lead that connects to a first pole of an AC power source and (ii) a one or more auxiliary leads; wherein the power cable includes a dual core having the primary lead on a first side and the one or more auxiliary leads on a second side with a web being located between the first side and the second side.

The present teachings provide: An electrosurgical device: (a) first power cable comprising: (i) a primary lead that is configured to connect to a first pole of an AC power source; (ii) one or more auxiliary leads; and (b) a second power cable comprising: (i) a return lead that connects to a second pole of the AC power source; wherein the first power cable includes a dual core having the primary lead on a first side and the one or more auxiliary leads on a second side.

Another possible embodiment of the present teachings comprises: an electrosurgical device comprising: (a) a power cable comprising: (i) a primary lead that is configured to connect to a first pole of an AC power source; (ii) one or more auxiliary lead; and (iii) one or more shields; wherein the one or more shields are electrically conductive, wherein the one or more shields are electrically connected to a second pole of the AC power source and all or a portion of a length of the primary lead, the one or more auxiliary leads, or both are surrounded by the one or more shields.

The teachings herein provide an electrosurgical device with a power cord that prevents capacitive coupling. The present teachings provide an electrosurgical device that has a multi-core and each of the cores are separated by a web that spaces the cores apart. The present teachings provide an electrosurgical device where one or more of the leads have a portion that is covered by a shield so that the shield prevents power from transferring form a powered lead to a non-powered lead. The present teachings provide an electrosurgical device where the shield is electrically connected to a ground or a lead that is connected to a second pole of an AC power source so that power from an active lead is dissipated without being transferred to an off or disconnected lead. The present teachings provide an electrosurgical device with three or more leads and at least two of the leads are spaced a sufficient distance apart so that the leads are not capacitively coupled.

DETAILED DESCRIPTION

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to an electrosurgical device. Preferably, the present teachings relate to an electrosurgical device with a power cord and associated componentry that form an electrosurgical system. The electrosurgical system may be any system that includes one or more of the devices taught herein. Preferably, the electrical surgical system includes at least an electrosurgical device. The electrosurgical system may include one or more electrosurgical devices with a hand piece as taught herein, one or more ground pads, one or more generators, one or more adjacent hand piece components, or a combination thereof and the teachings herein of each device which are incorporated into the electrosurgical system.

The electrosurgical device may function to be used by a surgeon to perform a surgical procedure. The electrosurgical device may function to be switched between two or more configurations, two or more states, or both. For example, the electrosurgical device may be switched between a monopolar configuration, a bipolar configuration, a non-electrosurgical configuration, or a combination of the three. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate, fulgrate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, the like, or a combination thereof. In another example, one or more parts of the electrosurgical device may include a sharp edge and may be used to cut, similar to that of a scalpel. The electrosurgical device may include a hand piece and a generator. The electrosurgical device may have one or more therapy signals that extend between the hand piece and the generator.

The one or more therapy signals may be a signal, power, continuity, or a combination thereof. The one or more therapy signals may extend from the hand piece to the generator or vice versa. Preferably, the therapy signals extend between the generator and one or more electrodes located on or in electrical communication with the hand piece or generator through one or more leads in a power cable. The one or more therapy signals may be formed by the hand piece, formed by the generator, or both. The electrosurgical therapy signals may be a therapy current. Preferably, the electrosurgical therapy signals indicate that a user has performed a step and a signal is being transmitted so that therapy current, energy, or both is generated. The electrosurgical therapy signals may provide a signal so that one or more therapy currents are produced and the therapy currents may be used for electrosurgery. The electrosurgical therapy signal may be a monopolar therapy signal, a bipolar therapy signal, or both. The monopolar therapy signal may be any signal that has a voltage differential between a return port and an active port in the generator. The monopolar therapy signal may be any signal that when applied by the electrosurgical device extends from one electrode of an electrosurgical device to another electrode of the electrosurgical device that is located at a remote location, off of the electrosurgical device, off the hand piece, or a combination thereof. The bipolar therapy signal may be any signal that has a voltage differential between two leads that are connected to the electrosurgical device, that are located in the generator, or both. The bipolar therapy signal may be any signal that when applied by the electrosurgical device extends from one component of a hand piece to another component of the hand piece (e.g., between two working arms, from a blade electrode to one or both working arms, or both). The therapy signal may be generated and conducted from the generator to the hand piece and then returned to the generator.

The generator may be any device that supplies power, a therapy current, control signals, an electrosurgical therapy signal, electronically reconfigures itself in response to a signal from the user, physically reconfigures in response to adjustments by the user, or a combination thereof. The generator may function to be electrically connected to an electrosurgical device to provide and/or receive electrosurgical therapy signals, power, therapy current, or a combination thereof. The generator may be capable of producing only a single therapy current. The generator may be capable of producing two therapy currents. The generator may include two or more power connections, three or more power connections, or four or more power connections. The generator may include one or more power sources. The generator may include two or more power sources. The generator may include a primary power source and an auxiliary power source. The power connections may be any port in the generator so that one or more power connectors of the power cable may be plugged into so that power, control signals, therapy currents, or a combination thereof are supplied to the electrosurgical device. The generator may include one or more switches that may be switched between one or more of the power connections so that power, signals, or both may be selectively applied to the electrosurgical device based upon a desired configuration of the electrosurgical device. The generator may supply power to an electrosurgical device through one or more power cables that include one or more plugs.

The one or more plugs may function to supply a therapy signal to a power cable and then to an electrosurgical device. The one or more plugs may function to connect a power cable to a generator. The one or more plugs may each provide a different therapy signal. For example, one plug may connect to a port of a generator to provide a bipolar therapy signal and one plug may connect into a port of a generator to supply a monopolar therapy signal. The one or more plugs may connect to a core of a power cord and at the plugs the cores may be located a distance apart. The cores as they extend away from the plugs may remain separate or the cores may be combined to form a multi-core power cable.

The one or more power cables may function to provide a therapy signal from the generator to an electrosurgical device, to return a therapy signal from an electrosurgical device (e.g., one or more electrodes on an electrosurgical device) back to the generator, or both. The one or more power cables may include one or more cores (e.g., a group of one or more leads). Each power cable may have a plurality of cores. The power cable may be a dual core cable having discrete cores that are located a distance apart along their entire length and connected by a web. The power cables may be a power supplying power cable (I.e., a first power cable), a power returning power cable (i.e., a second power cable), or both. A first power cable may be connected to a first port (e.g., an active port). A second power cable may be connected to a second port (e.g., a return port). The power supplying power cable may be free of return leads. Preferably, when a return lead is used the return lead is in a second separate cable from the primary leads and the auxiliary leads. The power supplying power cables and the power returning power cables may be discrete from each other. The power supplying power cable, the power returning power cables, or both may include one or more cores, one or more leads, or both. The power cable may have cores that are combined together to form a single power cable along a length of the power cable. The power cable may be a multi-core cable. The multi-core cable may have three or more, four or more, five or more, or even six or more cores that include one or more leads within each of the cores. Preferably, the power cable is a dual core cable. A return cable may be a single core cable.

The cores may function to carry one or more leads. The cores may be a combination of one or more leads. When multiple leads are located within a core the leads may be individually insulated relative to each other. When multiple leads are located within a core the leads may not be individually insulated but may be separated by an insulative layer or a shield. The core may be a section of a power cable that comprises one or more conductive leads that are in close proximity and surrounded by a common outer jacket. Each of the cores of the power cable may include one or more leads. Each core may include two or more leads, three or more leads, four or more leads, or even five or more leads. The power cables when connected together have cores (and leads) that are located a distance apart. The cores, leads, or both may be located a sufficient distance apart so that a therapy signal (e.g., energy (e.g., current, voltage, power, signals, or a combination thereof)) is restricted or prevented from passing from one core, lead, or both to an adjacent core, lead, or both. For example, the cores may include one or more webs, one or more shields, or both that resist energy from passing between cores or leads. The one or more webs, one or more shields, or both may increase resistance, impedance, or both between two or more leads so that an amount of power realized by an adjacent lead is reduced, or prevented, when compared to a power cable that does not include the one or more webs, the one or more shields, or both. The one or more webs increases impedance between two or more cores, two or more leads, or both so that an amount of energy transferred between the cores or the leads is reduced when compared to a power cable without webs. The one or more webs, one or more shields, or both may resist about 10 percent or more, about 20 percent or more, about 30 percent or more, about 40 percent or more, or about 50 percent or more from extending between two cores or two leads. The one or more webs, one or more shields, or both may resist 100 percent or less of the energy from passing between two cores or two leads. The cores, leads, or both may be located a distance apart so that substantially no energy is coupled from one core, lead, or both to an adjacent core, lead, or both (about 40 percent or less ±10 percent is transmitted from one lead to an adjacent lead). The distance may be sufficient large or wide so that an amount of energy that is coupled from a primary lead to an auxiliary lead is about 0.5 percent or less, preferably about 0.3 percent or less, about 0.2 percent or less, or about 0.1 percent or less the energy of the primary lead. Preferably, each core of the power cable includes one or more leads and the one or more leads provide power from a generator to an electrosurgical device.

The one or more leads function to carry one or more therapy signals (e.g., current or voltage) from a generator through the power cable and to an electrode. The one or more leads may be a conductive material. The one or more leads may be metal. Preferably, the one or more leads are one or more copper wires. The one or more leads may be a plurality of wires. The one or more leads may be a solid copper wire. The one or more leads may be a plurality of braided copper wires. The one or more leads may carry a bipolar therapy current, a monopolar therapy current, or both. The one or more leads may be physically disconnected, electrically disconnected, electrically disabled, physically disabled, or a combination thereof. The one or more leads may be free of power directly from the generator. The one or more leads may include an electric terminal. The electric terminal may function to connect a lead to another device. The electric terminal may function to connect a lead to the plug, the electrode, or both. The electric terminal may be a joint. The electric terminal may be a mechanical connection, an electrical connection, or both. The electric terminal may be solder, a weld, a conductive adhesive, a female part, a male part, or a combination thereof. The one or more leads may form a core of the power cable. The one or more leads may be a primary lead, a return lead, an auxiliary lead, a shunt lead, or a combination thereof.

The one or more primary leads may function to supply a therapy current to a feature of interest, an electrode, or both. The one or more primary leads preferably supplies a monopolar therapy current. Preferably, the one or more primary leads are connected to an alternating current (AC) power source. The one or more primary leads may have a first end connected to the AC power source and a second end connected to an electrode. For example, a proximal end of the primary lead may be connected to generator and a distal end of the primary lead may be connected to an electrode. The one or more primary leads may be a lead connected to an electrode that supplies a therapy current that extends through the electrode, into tissue, and then to a return electrode, return lead, or both that are located at remote location relative to the primary lead, the electrode of the primary lead, or both. The primary lead may be located in a separate power cable from a return lead. The primary lead may be a powered lead (i.e., a lead electrically connected to a pole or a power supply). The primary lead may be located proximate to one or more auxiliary leads.

The one or more auxiliary leads may function to supply a therapy current, power an electrode, power an electronic element (e.g., a non-therapeutic electrode), or a combination thereof. The one or more auxiliary leads may pass through the same core or a separate core of a power cable than a primary lead. The one or more auxiliary leads may be disconnected, have an open circuit, be turned off, not powered, not connected, or a combination thereof from a pole. The one or more auxiliary leads may have a section that is exposed to a primary lead (i.e., a powered lead), have an exposed electrode, or both. The one or more auxiliary leads may change in function as the functions of the electrosurgical device change. The one or more auxiliary leads may supply a bipolar therapy current, power a light, power a light emitting diode (LED), power a switch, power a thermocouple, or a combination thereof. The one or more auxiliary leads may be located within the same power cable as a primary lead but in a different core of the primary lead. The one or more auxiliary leads may be a plurality of auxiliary leads. A power cable may include 2 or more, 3 or more, 4 or more, or even 5 or more auxiliary leads. The auxiliary leads may be an electrical lead. The plurality of auxiliary leads may extend through one core. Each of the plurality of auxiliary leads may extend through an individual core. The auxiliary leads, the primary leads, or both may be located within a different power cable than the one or more return leads. The one or more auxiliary leads, one or more primary leads, or both may include a shield that extend over a portion thereof and the shield may be connected to one or more shunt leads.

The one or more shunt leads may function to reduce or remove stray current from passing from the primary lead to the auxiliary lead. The one or more shunt leads may be connected to a shield. The one or more shunt leads may connect a shield to a return lead. The one or more shunt leads may reduce or remove capacitive coupling between two adjacent leads. The one or more shunt leads may be electrically connected to a second pole of an AC power source. The one or more shunt leads may be electrically connected to a second pole of an AC power source via one or more return leads. The one or more shunt leads may extend through a portion of power cable. The one or more shunt leads may extend along a core or from one core or lead to another core or lead. The one or more shunt leads may connect a shield to a return lead.

The one or more return leads may function to complete a circuit. The one or more return leads may be connected to a second pole of an AC power source. The one or more return leads may complete a circuit for the primary lead. The one or more return leads may connect a ground pad, a shield, or both to a second pole of an AC power source. The one or more return leads may be connected to a return electrode. The one or more return leads may be connected to a ground pad. The one or more return leads may be located in a separate power cord from the auxiliary lead, the primary lead, or both. The one or more return leads may be located within a power cable with a single core.

Each power cable may include one or more cores. The power cables may include three or more, four or more, or even five or more cores. Each core may contain one or more leads, two or more leads, three or more leads, four or more leads, or even five or more leads. Each of the cores may be covered by an outer covering (e.g., a jacket) of the power cable. Each of the cores may be fully or partially covered by a shield. Each of the cores may be separated from an adjacent core by a web, one or more cores, or both.

The one or more webs may function to create a space, a dielectric space, a distance, or a combination thereof between two or more cores, two or more leads, or both. The one or more webs may be an extension of an outer covering of the power cable. The one or more webs may be a bridge that extends between a first core and a second core and connects the first core to the second core. The one or more webs may be sufficiently large to restrict or prevent power from extending from one lead to an adjacent lead. The one or more webs may create a sufficient distance (e.g., width) so that power is restricted or prevented from passing from one core or lead to an adjacent core or lead. The one or more webs may be sufficiently large so that power transferred from a lead to an adjacent lead is below a threshold value. The one or more webs may be sufficiently large so that power transferred from a lead to an adjacent lead is substantially free of power being transferred (e.g., about 4.5 W or less). A threshold value of power transferred from one lead to another lead may be about 10 W or less, about 5 W or less, preferably about 3 W or less, or more preferably about 1 W or less. The one or more webs may have a length or width and the length or width may be the distance between a first core and a second core. The distance of the web may be sufficient large or wide so that therapy signals are prevented from passing from the first core to the second core, or from a core to an adjacent core. The distance of the web may be about 4 mm or more, about 5 mm or more, about 6 mm or more, about 7 mm or more, or even about 8 mm or more less when measured from a center of one core to a center of an adjacent core. The distance of the web may be about 10 cm or less, about 5 cm or less, or about 2 cm or less when measured from a center of one core to a center of an adjacent core. The one or more webs may be sufficient thick and wide that the one or more webs provide support between the first core and the second core. The web may be sufficient thick so that the first core and the second core cannot be bent into contact with each other. The web may have a distance of about 0.1 mm or more, about 0.2 mm or more, about 0.5 mm or more, or about 1 mm or more. The web may have a distance of about 5 mm or less, about 4 mm or less, or about 2 mm or less. The cord may have a length of about 1 m or more, about 2 m or more, or about 3 m or more. The cord may have a length of about 10 m or less, about 7 m or less, or about 5 m or less. The cord may have a wire with a gauge of about 15 or more, about 20 or more, about 25 or more, or about 30 or more measured using American wire gauge (AWG). The cord may have a wire with a gauge of about 50 or less, about 40 or less, about 35 or less measured using American wire gauge (AWG). The cord may have a gauge of between about 30 and 32 measured using American wire gauge (AWG). Thus, for example a power cord that is 3 m long with wires with a gauge of about 30 may need a web distance of about 8 mm to have about 4.5 W or less transfer from a primary lead to an auxiliary lead. The web may be sufficiently large so that a capacitance (e.g., threshold capacitive value) between a primary lead and an auxiliary lead are about 200 pF or less, about 100 pF or less, preferably about 75 pF or less, more preferably about 60 pF or less, and most preferably about 50 pF or less. The web may be part of the outer covering.

The outer covering (e.g., jacket) may function to prevent power from leaving the leads. The outer covering may prevent a dielectric barrier around each core, the leads, or both. The outer covering (e.g., jacket) may cover the one or more cores, the one or more leads within the one or more cores, or both. The outer covering may be formed around the one or more leads. The outer covering may be formed and then the one or more leads inserted into the outer covering. The outer covering may be made of a polymeric material, a flexible material, a material with insulative properties, or a combination thereof. Preferably the outer covering protects the leads. The outer covering may be made of a thermoplastic polyurethane, a fluorinated ethne propylene, or both. The outer covering may connect two or more cores together, two or more leads together, or both into a single power cable. The outer covering may be made of rubber, an elastomer, plastic, a polymer, a dielectric material, or a combination thereof. The outer covering may cover or include a shield that extends around one or more of the cores, the leads, or both.

The one or more shields may function to restrict or prevent therapy signals (e.g., power, voltage, current, or a combination thereof) from extending form one lead to an adjacent lead. The one or more shields may be connected to a return lead. Preferably, the one or more shields are electrically connected to a return lead via one or more shunt leads. The one or more shields may be connected to a ground or a second pole of an AC power source by one or more shunt leads. The one or more shields may interrupt a current leak from a primary lead so that the shield prevents an auxiliary lead from being capacitively coupled to a primary lead. A primary lead and an auxiliary lead may be constructively capacitively coupled together and the functional capacitively coupling may be about 1 pF or more and preferably about 2 pF or more. The one or more shields may be capacitively coupled to a core, one or more leads in a core, or both. The one or more shield may be electrically coupled to a second pole of an AC power source, a return lead, or both. Capacitively coupling may be electrically coupling, but is not conductively coupled. Preferably, electrically coupling is an electrical connection that is conductively coupled. The shield may be coupled to one or more leads so that power is differentially passed to the shield and then differentially passed from the shield, the return lead, or both to the second pole so that the shield restricts or prevents current from being capacitively transferred to the one or more auxiliary leads. The one or more shields may surround a portion of a core, a lead, or both. The one or more shields may cover substantially an entire length of one or more leads. The one or more leads may extend around one or more, two or more, three or more, or even four or more of the leads in a power cable. The one or more shields may extend around one or more cores, two or more cores, three or more cores, or even four or more cores (and the leads within the cores). Each shield may extend around only one core. Each shield may extend around one or more or a plurality of leads located within a core. Each shield may extend around only one lead. The one or more shields may be sufficiently long, thick, conductive, or a combination thereof to restrict or prevent power from extending from one lead to an adjacent lead. The one or more shields may be sufficiently long, thick, conductive, or a combination thereof so that power transferred from a lead to an adjacent lead is below a threshold value. The one or more shields may be sufficiently long, thick, conductive, or a combination thereof so that power transferred from a lead to an adjacent lead is substantially free of power being transferred (e.g., about 4.5 W or less). A threshold value of power transferred from one lead to another lead may be about 10 W or less, about 5 W. or less, preferably about 3 W or less, or more preferably about 1 W or less. A threshold value of power transferred may be below a leak current threshold (e.g., testing using International Electrotechnical Commission for electrical devices). The shield may be sufficiently long, thick, conductive, or a combination thereof so that a capacitance (e.g., threshold capacitive value) between a primary lead and an auxiliary lead are about 200 pF or less, about 100 pF or less, preferably about 75 pF or less, more preferably about 60 pF or less, and most preferably about 50 pF or less. The shields may be made of metal, plastic, a dielectric, a ceramic, a conductive material, a non-conductive material, or a combination thereof. Preferably, the shield is made of a conductive material and during operation therapy signals from a lead are transferred (e.g., by capacitive coupling) to the shield and then the therapy signals are dissipated from the shield by a shunt lead. The shield may prevent power from passing from one lead to an adjacent lead by the shield dissipating all or substantially all of the therapy signal instead of the therapy signal extending to the adjacent lead. Each shield may be connected to one or more shunt leads.

The one or more shunt leads may function to complete a circuit so that some power is dissipated from the shield without all of the power reaching the lead within the shield covers. The shunt lead may be a lead that extends between the shield and a lead that is connected to the remote electrode, the power source, or both. The shunt lead may direct a therapy signal or a stray therapy signal (e.g., an unintended power flow) away from electrodes that are a part of the electrosurgical device. The shield, the shunt lead, or both may prevent capacitive coupling.

Capacitive coupling may be power that extends from a powered lead to a non-powered lead. Capacitive coupling may power an electrode that is not intended to be powered. Capacitive coupling may be an unintentional flow of power from a lead or an electrode. Capacitive coupling may allow for power to extend from a lead that is connected to a power source to extend to a lead that is disconnected from the power source or disabled from being powered by the power source. The power source may include a first pole and a second pole. The first pole may be a positive side or a negative side of the power source. The second pole may be an opposite polarity as the first pole. For example, if the first pole is negative then the second pole is positive. The capacitive coupling may power one or more electrodes if the energy generated by the capacitive coupling is not limited, controlled, or eliminated. The capacitive coupling may extend from one lead to an adjacent lead and power an electrode, an electronic element, or both connected to the adjacent lead when the capacitive coupling is not limited, controlled, or eliminated.

The electrodes, electronic element, or both may be any device that is connected to a lead and assists an electrosurgical device in working when power is applied through the lead. The electrodes may pass a bipolar energy, monopolar energy, or both between electrodes. The electrodes may be part of the electrosurgical device. The electrodes may be connected to a hand piece. The electrodes may be on one or more working arms of a hand piece, a blade electrode, of both. The electrodes may be an electronic element (e.g., a non-therapeutic electrode). The electronic elements may be electrodes that assist in a procedure without directly being used to electrically treat a location of interest (e.g., tissue). The electronic elements may be connected to any lead (e.g., primary lead, auxiliary lead, a return lead). The electronic elements may be a light, a light emitting diode (LED), a switch, a thermocouple, or a combination thereof. The electrode may be located remote from a hand piece. The electrode may be a ground pad. The ground pad electrode may be used in condition with the blade electrode. The electrodes may be part of a first device, a second device, a third device, or a combination thereof. Each of the leads may be connected to a single electrode. Two leads may be connected to one electrode. For example, a LED may be connected to two leads. Preferably, the electrosurgical device includes electrodes on the working arms, a blade electrode, and a ground pad.

The working arms may be connected to and extend from a hand piece. The working arms may function to grip, hold, squeeze, or a combination thereof an object when the object is between the two or more opposing working arms. The working arms may move in a single plane towards and away from each other. The working arms may include one or more gripping features that may assist in gripping, holding, squeezing, or a combination thereof an object. The working arms may be movable between two or more positions. Preferably, the working arms are movable between at least a first position and a second position. For example, the working arms may be movable between a bipolar configuration (e.g., first position) and a monopolar configuration (e.g., second position). The working arms in the first position may be off, energized, one working arm may be energized, or a combination thereof. The electrodes on the working arms may be energized when the working arms are energized. The working arms in the second position may be off, one or both of the working arms may be electrically disconnected, one or both of the working arms may be electrically connected, one working arm may be shorted by the other working arm, one or both arms may be electrically disabled, or a combination thereof. More preferably, in the second position the working arms are immobilized so that the working arms cannot be used as forceps. The working arms may be longitudinally static and moveable relative to each other. The working arms may be longitudinally moveable and may be moveable relative to each other so that a gripping force may be created. For example, the working arms when in a bipolar configuration may both be extended and then retracted so that a blade electrode may be exposed forming a monopolar configuration. The working arms may be retractable and/or extendable individually, simultaneously, or both. The working arms may be selectively retractable and/or extendable so that one or more tip regions are exposed.

The working arms may include a tip region. The tip region may include a portion that is configured to assist in facilitating gripping, holding, squeezing, or a combination thereof. Additionally, the tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. Preferably, the tip region includes insulation on the non-contact portions of the working arms so that electrosurgical energy is not transferred through incidental contact. The contact portions of the tip region may include one or more electrodes. The working arms may include an active portion and an inactive portion (i.e., an insulated portion).

The active portion (e.g., electrodes) may function to apply power. The active portion may be the same portion as the contact regions of the forceps. Thus, for example, when tissue is grasped between the contact portions of the forceps, power may be supplied to the tissue through this contact portion. The active portion of the working arms preferably is between the two opposing working arms and the active portion of the blade electrode is the portion that extends beyond the working arms, out of the channel, or both. The active portions may be substantially surrounded by inactive portions or portions that are insulated. The inactive portion may be any portion that does not supply power, that is insulated, or both. The inactive portion may be any portion that may transfer power through incidental contact and thus are insulated so that incidental transfer of power does not occur and/or stray current is prevented. For example, an outside of the working arms may be coated with an insulating material so that if the working arms accidentally contact tissue proximate to the tissue of interest the proximate tissue is not subjected to a transfer of power. The inactive portion and the active portion may be made of different materials, coated with different materials, or both.

The blade electrode may be any device that may be used to apply monopolar power during a procedure, that may be longitudinally movable, rotationally movable, extendable, retractable, or a combination thereof. The blade electrode may be static. Preferably, in one embodiment the blade electrode may be static and the working arms moved relative to the blade electrode so that when the working arms are moved the blade electrode is exposed. More preferably, the blade electrode is a movable. The blade electrode may have a first position (e.g., retracted) and a second position (e.g., extended). The first position may be where the blade electrode is located relative to the working arms so that the working arms are past the blade electrode (e.g., the blade electrode is retracted so that the working arms extend past the blade electrode or the working arms are extended so that the working arms extend past the blade electrode). The first position may be where the blade electrode is electrically disconnected, electrically shorted relative to another hand piece component, electrically insulated so that power cannot pass from the blade electrode, or a combination thereof. The second position may be where the blade electrode is located relative to the working arms so that the blade electrode (e.g., at least the electrode on the blade electrode) is extended beyond the working arms (e.g, the blade electrode is extended so that the working arms are located proximate to the user or the working arms are retracted so that the blade electrode is beyond the working arms). The second position may be where the electrode of the blade electrode is electrically connected, supplies a therapy current, is electrically continuous, or a combination thereof. The blade electrode may be a separate piece that when activated may be used to supply monopolar power. The blade electrode may be formed by connecting the two working arms together and supplying power through only one working arm. The blade electrode may be used for electrically cutting, mechanically cutting, or both. The blade electrode may be a discrete third working arm that may extend from one of the working arms, between the working arms, or both. The blade electrode may extend longitudinally beyond the working arms so that power may be supplied from the electrode without the electrodes on the working arms being in contact with tissue being treated.

The monopolar insulator may be any device that may insulate all or a portion of the active portions of the working arms. The monopolar insulator may prevent the working arms from contacting the blade electrode when the electrosurgical device is in the bipolar configuration. The monopolar insulator may be moved into contact with one or both of the working arms and immobilize the working arms so that the working arms cannot be used as forceps. The monopolar insulator may prevent power from being transferred from one or both of the working arms to the blade electrode. The monopolar insulator may prevent stray current from being conducted from the working arms to a surrounding area, the blade electrode, the ground pad, or a combination thereof. During a change from a bipolar configuration to a monopolar configuration the monopolar insulator may extend between the working arms and once past the working arms a bias device may act to retract the monopolar insulator so that the tips of the working arms are pressed into a portion of the monopolar insulator and immobilized.

The blade electrode may be any part of the electrosurgical device that supplies power from one location and the power extends to a distal location. The blade electrode may be a combination of two or more devices that when combined may form a blade electrode. The blade electrode may be a discrete part that when electrically powered provides power. The blade electrode may be static, rotatable about its axis, longitudinally movable about its axis, or a combination thereof. The blade electrode may be blunt, have one or more sharpened edges, have dull edges, or a combination thereof. The blade electrode may rotate to any angle so that the blade electrode may be used to cut, be ergonomically oriented so that a user is not required to reposition their grip, used for vertical cutting, used for side to side cutting, or a combination thereof. The blade electrode may be rotated so that a height of the blade electrode forms an angle with the active portion of the working arms. A height of the blade electrode and the active portion may form an angle of about 15 degrees or more, about 30 degrees or more, about 45 degrees or more, about 60 degrees or more, or even about 90 degrees or more. The height of the blade electrode may be rotated at an angle of about 275 degrees or less, about 225 degrees or less, about 205 degrees or less, or about 180 degrees or less with the active portion of the working arms. For example, the blade electrode may have a height and the height may be parallel to the active portions of the working arms and the blade electrode may be rotated so that the height is perpendicular to the active portions of the working arms. The blade electrode may maintain a complete circuit during rotation so that power may be applied through the blade electrode as the blade electrode is rotated.

The blade electrode, the bipolar electrode (e.g., electrodes on the working arms), or both may complete a circuit when in contact with tissue. The bipolar electrode may have two opposing working arms and the tissue may electrically connect the working arms, form an electrical bridge between the two arms, or both. The blade electrode may have a single blade electrode (i.e., a monopolar working arm) and the tissue may electrically connect the blade electrode with a return electrode, act as an electrical bridge between the blade electrode and the return electrode, act as an electrical bridge between the blade electrode and one or both of the bipolar electrodes, or a combination thereof. The blade electrode when extended may activate a circuit, a switch, or both. The blade electrode when retracted may be disconnected, disabled, or both and capacitive coupling may be prevented, reduced, or eliminated from powering the blade electrode by a shield, a web, a length, or a combination thereof. The electrodes of the first working arm and the second working arm may be disconnected, disabled, or both when the blade electrode is extended beyond the first working arm, the second working arm, or both and capacitive coupling may be prevented, reduced, or eliminated from powering the first working arm, the second working arm, or both by a shield, a web, a length, or a combination thereof.

The hand piece may be any part of the device that the user grips, that houses one or more of the control buttons, one or more switches, one or more electrical connectors, one or more diodes, one or more capacitors, or a combination thereof. The hand piece may house all or a portion of the control circuitry, a central processing unit, or both. The hand piece may electrically connect the electrosurgical device, the electrical system, or both to the generator. The hand piece may connect to one or more power cables. Preferably, the hand piece is connected to a single power cable that provides two or more different therapy signals (e.g., monopolar energy and bipolar energy). The hand piece may both physically connect the electrodes of the electrosurgical device and electrically connect the electrodes of the electrosurgical device to a power source, a power cable, or both. The hand piece may be a body portion of the electrosurgical device, a portion between the two or more working arms, a connector between the two or more working arms, that houses all or a portion of the circuitry that includes an activation circuit that includes one or more control buttons, or a combination thereof. Preferably, the hand piece is the portion that a surgeon grips and presses one or more buttons to apply power to a desired location. More preferably, the hand piece is a central portion that includes both buttons and one or more electrical connectors for supplying power to the electrosurgical device, the working arms, the blade electrode, or a combination thereof. The hand piece may include one or more movable members, one or more hand piece components, or both. The working arms, blade electrode, light emitting diodes, switches, thermistors, or a combination thereof may be located within or on the hand piece.

Figure 1:
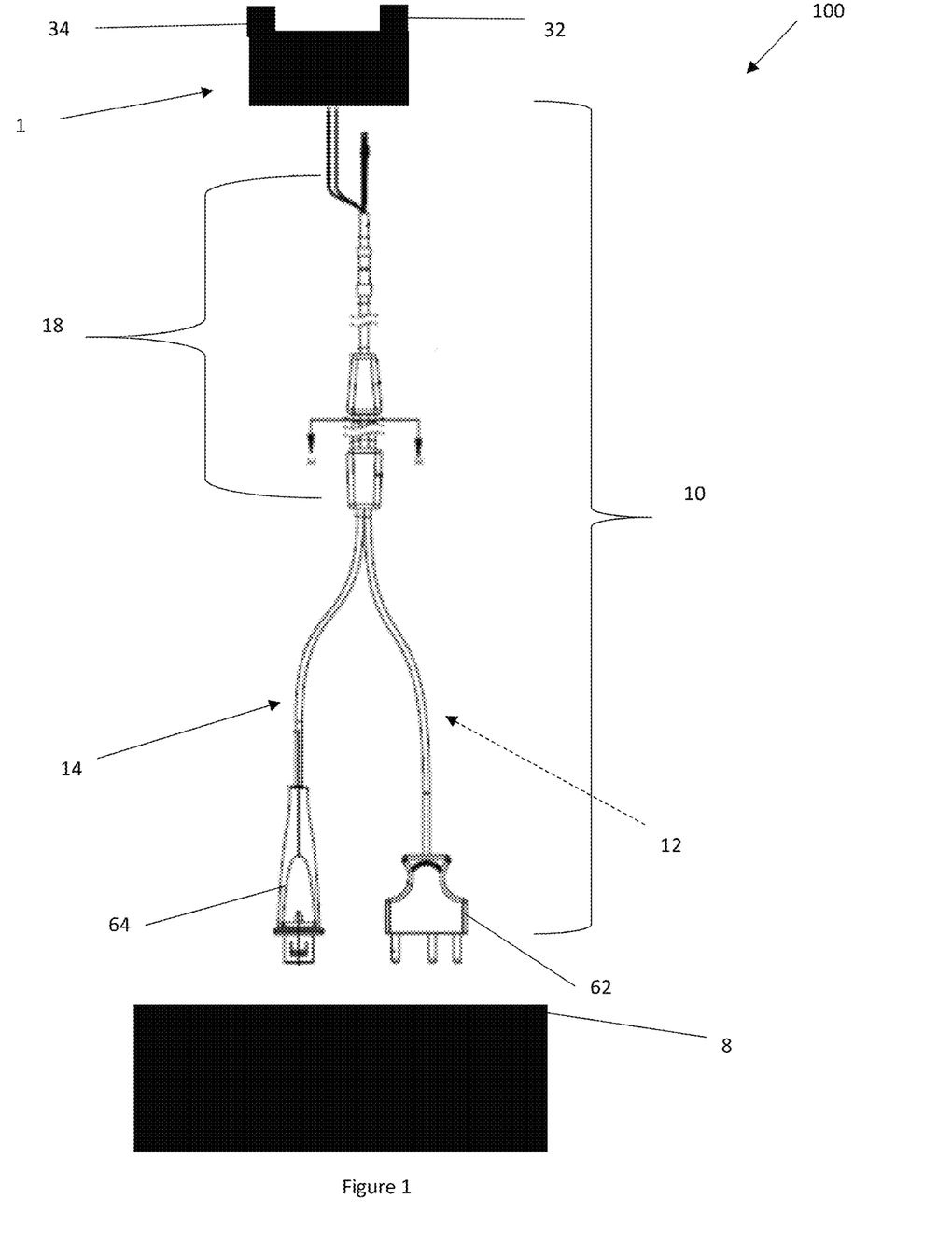
FIG. 1 illustrates an electrosurgical system.

FIG. 1 illustrates an electrosurgical system 100 with a power cable 10 that extends between a generator 8 and an electrosurgical device 1. The power cable 10 includes a primary lead 12 having a first plug 62 and an auxiliary lead 14 with a second plug 64 that connect to the generator 8. The primary lead 12 and the auxiliary lead 14 are combined together in a multi-core cable 18 or at least a section of the multi-core the cable 18. The primary lead 12 supplies a therapy current to a first electrode 32 so that the electrosurgical device 1 provides a therapy current to a desired region, and the auxiliary lead 14 is not powered and does not supply a therapy current to a second electrode 34.

Figure 2:
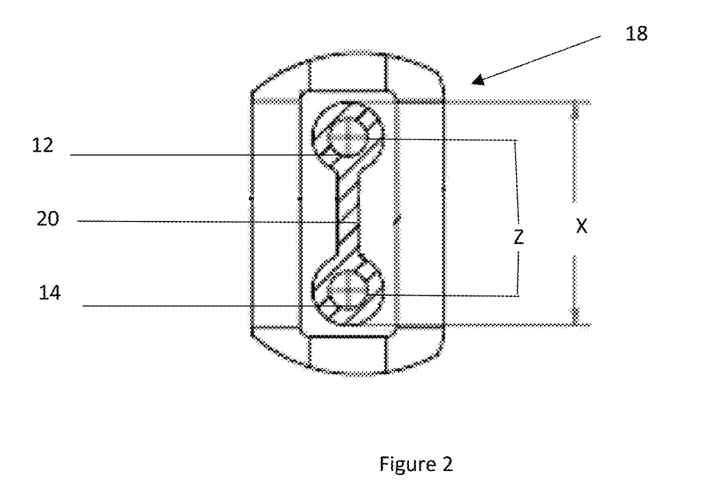
FIG. 2 is a cross-sectional view of the dual core power cord of FIG. 2 cut along line K-K.

FIG. 2 is a cross-sectional view of a section of the multi-core cable 18 of FIG. 1 cut along line K-K. The multi-core cable 18 includes a primary lead 12 on a first side of a web 20 and an auxiliary lead 14 on a second side of the web 20. The web 20 has a distance (Z) when measured from a center of the primary lead 12 to a center of the auxiliary lead 14 and the distance separates the primary lead 12 and the auxiliary lead 14. The primary lead 12, the auxiliary lead 14, and web 20 have a combined length (X).

Figure 3:
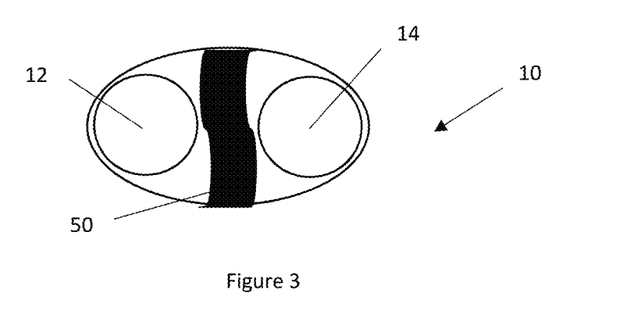
FIG. 3 illustrates a power cord with a shield extending between two leads.

FIG. 3 is a cross-section of a single core power cable 10 having a primary lead 12 and a auxiliary lead 14 that a separated by shield 50.

Figure 4A:
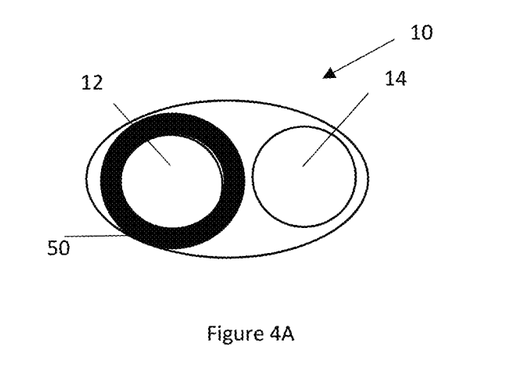
FIG. 4A illustrates a power cord with a shield extending around a primary lead.

FIG. 4A illustrates a cross-section of a single core power cable 10 with a primary lead 12 and an auxiliary lead 14 with the primary lead 12 being covered by a shield 50.

Figure 4B:
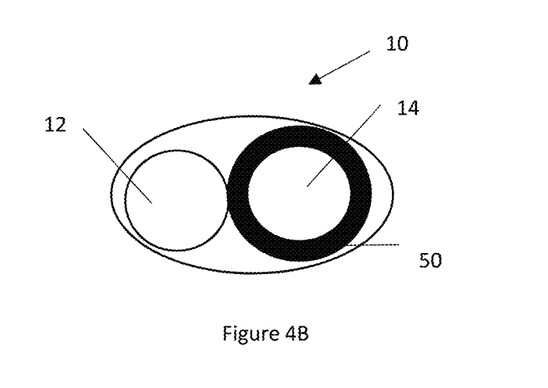
FIG. 4B illustrates a power cord with a shield around an auxiliary lead.

FIG. 4B illustrates a cross-section of a single core power cable 10 with a primary lead 12 and an auxiliary lead 14 with the auxiliary lead 14 being covered by a shield 50.

Figure 5:
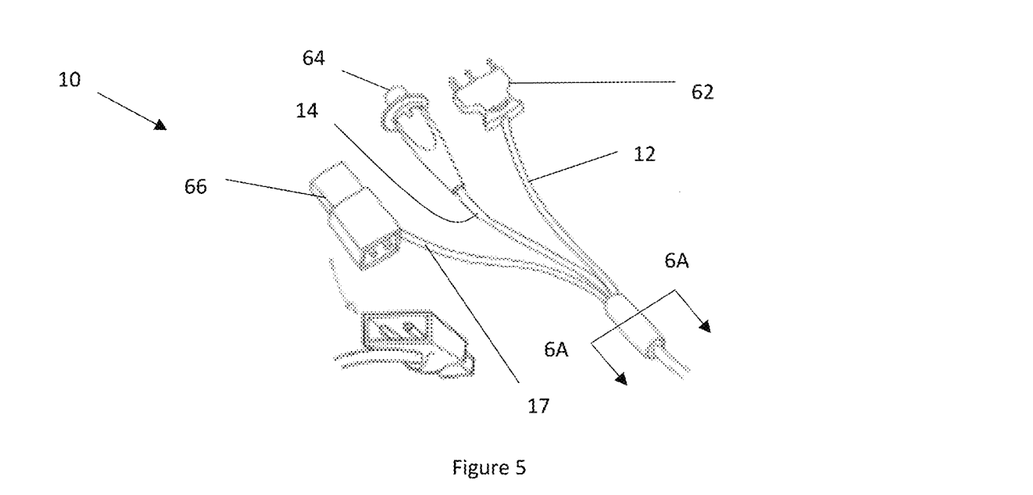
FIG. 5 illustrates a power cord with multiple connectors.

FIG. 5 illustrates a power cable 10 having a first plug 62 connected to a primary lead 12, a second plug 64 connected to a auxiliary lead 14, and a third plug 66 connected to a shunt lead 17. With an end of the third plug 66 being illustrated.

Figure 6:
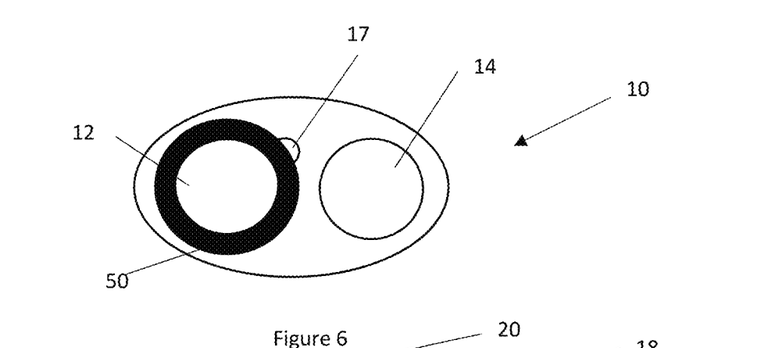
FIG. 6 illustrates a power cord with two leads and one lead covered by a shield that is connected to a second pole of an AC power source.

FIG. 6 is a single core power cable 10 where the primary lead 12 is covered by a shield 50. The shield 50 is connected to a return lead (not shown) by a shunt lead 17 and the auxiliary lead 14 is free of a shield.

Figure 7A:
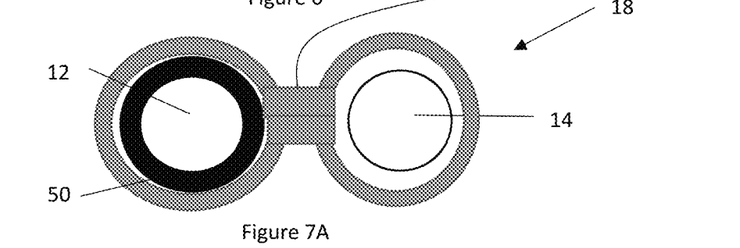
FIG. 7A illustrates a dual core power cord with a shield around one lead.

FIG. 7A illustrates a multi-core cable 18 where the primary lead 12 is covered by a shield 50 and the auxiliary lead 14 is free of a shield. The primary lead 12 and the auxiliary lead 14 being separated by a web 20.

Figure 7B:
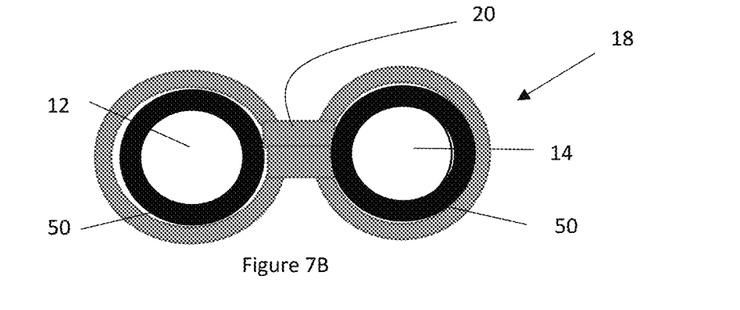
FIG. 7B illustrates a dual core power cord with a shield around both leads.

FIG. 7B illustrates a multi-core cable 18 where both the primary lead 12 and the auxiliary lead 14 are covered by a shield 50. The primary lead 12 and the auxiliary lead 14 being separated by a web 20.

Figure 8:
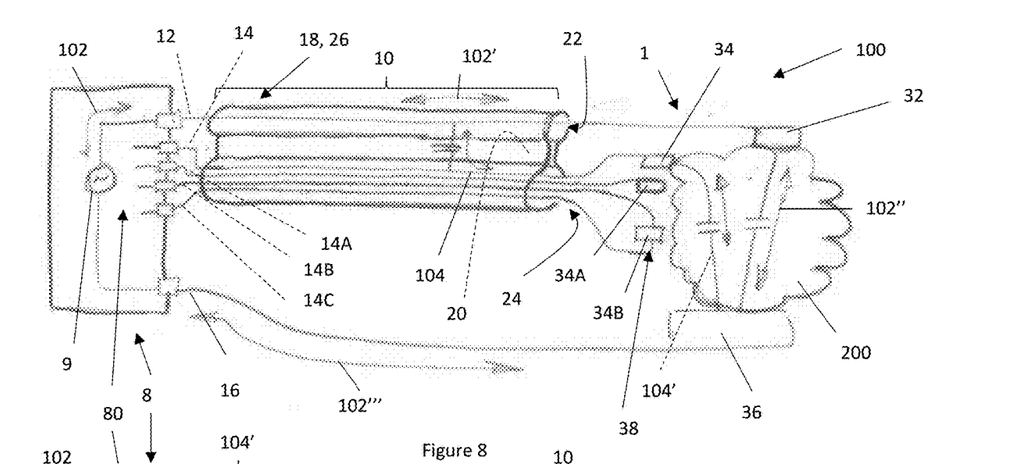
FIG. 8 is a schematic view an electrosurgical system having a dual core power cord with multiple leads extending though one core.

FIG. 8 is a schematic view of an electrosurgical system 100 that includes an electrosurgical device 1 that is connected to a generator 8 by a power cable 10. The power cable 10 is a multi-core cable 18 with an outer covering 26 (e.g., jacket). The generator 8 has a power source 9 that supplies a power flow 102 to the primary lead 12 that extends through a first core 22 of a multi-core cable 18. The power flow 102' continues through the primary lead 12 to the first electrode 32. The first electrode 32 is in contact with tissue 200 so that the power flow 102" follows an intended path through the tissue 200 to a return electrode 36. The multi-core cable 18 includes a second core 24 that includes a plurality of auxiliary leads 14, 14A, 148, and 14C. The plurality of auxiliary leads 14, 14A. 14B, and 14C all are disconnected from or disabled from receiving power form the power source 9, such as having have an open switch 80. The first core 22 and second core 24 are separated by a web 20. The auxiliary lead 14 is connected to an electrode 34, the auxiliary lead 14A is connected to an electrode 34A. The lead 14B and the lead 14C are connected to an electrode 348 that as shown is an electronic element 38. The web 20 has sufficient distance so that power is dampened from extending along an unintended flow path 104 between the leads in the first core 22 to the leads in the second core 24, however the unintended flow path 104 is shown for illustrative purposes. The unintended flow path would continue out the electrode 34 when the electrode 34 is in contact with tissue 200 so that the unintended flow path 104' extends to the return electrode 36. The power flow 102" would then flow through the return lead 16 along path 102''' to the generator 8 to complete a circuit.

Figure 9:
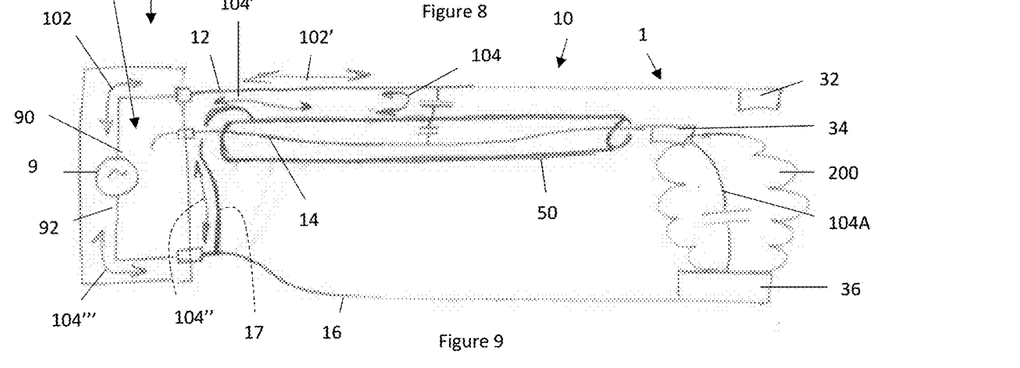
FIG. 9 illustrates a schematic view of an electrosurgical system having one lead shielded and demonstrating the unintended power path that is prevented by the shielding.

FIG. 9 illustrates a generator 8 connected to an electrosurgical device 1 by power cables 10. The power source 9 in the generator 8 creates a flow of power 102 from the first pole 90 that extends into the primary lead 12 and continues in the direction 102' to the first electrode 32. The primary lead 12 and the auxiliary lead 14 are located within a power cable 10 together and some or all of the power from the primary lead 12 is prevented from being transmitted to the auxiliary lead 14 by a shield 50. The auxiliary lead 14 is disabled from receiving power form the power source or disconnected from the power source, such as by having an open switch 80. The shield 50 is connected to a shunt lead 17 that is connected to the return lead 16 so that as power passes in the direction 104 from the primary lead 12 to the shield 50 the power continues in the direction 104' and 104" to the return lead 16 from the shunt lead 17. Finally, the power passes 104''' into the generator 8 and to the second pole 92 of the ac power source. The shield 50 being connected to the return lead 17 restricted or prevents the transmission of power along path 104A if the electrode 34 were to come into contact with tissue 200 so that a circuit was completed between the electrode 34 and the return electrode 36 when the auxiliary lead 14 is disconnected or disabled.

Figure 10:
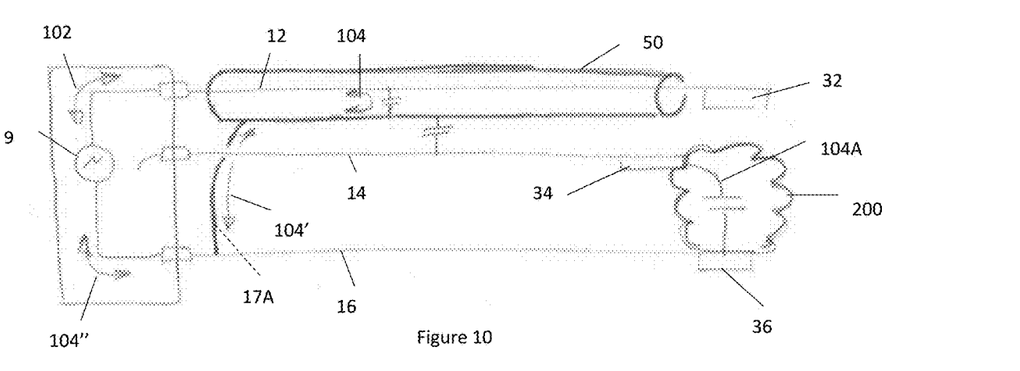
FIG. 10 illustrates a schematic view of an electrosurgical system with a primary lead shielded.

FIG. 10 illustrates the shield 50 being located on the primary lead 12 that is in connection with a first electrode 32, which is movable so that the first electrode 12 may be extended beyond the second electrode 34 (as shown) and retracted so that the second electrode 34 is distal of the first electrode 32 (not shown). As shown, power 102 is extending from the power source 9 to the primary lead 12 and the shield 50 restricts or prevents the power from moving to the auxiliary lead 14 and instead moves the power in the direction 104. The shield 50 is connected to a lead 17A that allows the power to flow in the direction 104' to the return lead 16 so that the power can be reverted back in the direction 104". The auxiliary lead 14 is disconnected or disabled and the shield 50 prevents power from traveling along path 104A from the second electrode 34 to the return electrode 36 through the tissue 200 and then back to the power source 9 through the return lead 16.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An electrosurgical device, comprising:
   a. a first power cable comprising:
      i. a primary lead that connects to a first pole of an AC power source;
      ii. a first auxiliary lead and a second auxiliary lead; and
      iii. an outer covering; and
   b. a second power cable comprising:
      i. a return lead that connects to a second pole of the AC power source;
   wherein the primary lead connects to a monopolar electrode of the electrosurgical device, the return lead connects to a return electrode of the electrosurgical device, and the first auxiliary lead and the second auxiliary lead connect to a first electrical terminal and a second electrical terminal, respectively;
   wherein the first auxiliary lead and the second auxiliary lead connect to an electronic element of the electrosurgical device to complete an electric circuit;
   wherein the first auxiliary lead and the second auxiliary lead connect to the AC power source through a switched connection to selectively disable the first and second auxiliary leads from receiving power; and
   wherein the first power cable includes a dual core, wherein a core is a group of one or more leads, the dual core having the primary lead on a first side within a first core and the first auxiliary lead and the second auxiliary lead on a second side together within a second core with a web being located between the first core and the second core.

2. The electrosurgical device of claim 1, wherein the web creates a sufficient distance so that a capacitance between the primary lead within the first core and the first and second auxiliary leads within the second core is below a threshold value.

3. The electrosurgical device of claim 2, wherein the threshold value is a capacitance of about 60 pF or less.

4. The electrosurgical device of claim 2, wherein the first and second auxiliary leads are substantially free of power from the primary lead when the primary lead is powered and the first and second auxiliary leads are free of power from the AC power source.

5. The electrosurgical device of claim 2, wherein the first and second electrical terminals are therapy electrodes and the first and second auxiliary leads are electrical leads.

6. The electrosurgical device of claim 2, wherein the first and second electrical terminals are connections between the first and second auxiliary leads and the electronic element of the electrosurgical device.

7. The electrosurgical device of claim 6, wherein the electronic element is an electrically powered element that is a thermocouple, a switch, a light emitting diode, or a combination thereof.

8. The electrosurgical device of claim 1, wherein the primary lead connects to a primary electrode, the primary lead and the return lead being connectable to the AC power source to provide a therapy current from the electrosurgical device.

9. The electrosurgical device of claim 1, wherein the web has a distance when measured from a center of the first core to a center of the second core, and the distance is about 5 mm or more.

10. An electrosurgical device comprising:
    a. a first power cable comprising:
       i. a primary lead that is configured to connect to a first pole of an AC power source; and
       ii. a plurality of auxiliary leads; and
    b. a second power cable comprising:
       i. a return lead that is configured to connect to a second pole of the AC power source;
    the first power cable including a dual core, wherein a core is a group of one or more leads, the dual core having the primary lead on a first side within a first core and the plurality of auxiliary leads on a second side together within a second core, wherein the first and second cores are spaced a distance apart along their entire length and connected by a web located between the first core and the second core;
    wherein the primary lead connects to a first electrode;
    wherein the return lead connects to a second electrode;
    wherein a first auxiliary lead of the plurality of auxiliary leads connects to a third electrode;
    wherein a second auxiliary lead of the plurality of auxiliary leads connects to a fourth electrode; and
    wherein a third auxiliary lead and a fourth auxiliary lead of the plurality of auxiliary leads connect to a fifth electrode.

11. The electrosurgical device of claim 10, wherein a therapy current is generated by the AC power source being transmitted from the primary lead through a volume of tissue to the return lead when both the first electrode and second electrode are in contact with the volume of tissue.

12. The electrosurgical device of claim 10, the first auxiliary lead of the plurality of auxiliary leads being connectable to the first pole of the AC power source and the second auxiliary lead of the plurality of auxiliary leads being connectable to the second pole of the AC power source to provide a therapy current from the electrosurgical device.

13. The electrosurgical device of claim 10, wherein the electrical terminal is a connection between the plurality of auxiliary leads and an electronic element of the electrosurgical device.

* * * * *